United States Patent [19]

Suga

[11] Patent Number: 4,519,716
[45] Date of Patent: May 28, 1985

[54] DEVICE FOR TESTING COMBUSTABILITY
[76] Inventor: Shigeru Suga, 20-2 Yoyogi 5-chome, Shibuya-ku, Tokyo, Japan
[21] Appl. No.: 598,456
[22] Filed: Apr. 9, 1984
[51] Int. Cl.³ ............................................. G01N 25/00
[52] U.S. Cl. .......................................... 374/8; 374/57; 219/494
[58] Field of Search ........................ 374/8, 43, 57, 210; 73/432 SD; 219/494, 505; 340/577–579, 589

[56] References Cited

U.S. PATENT DOCUMENTS 4,229,967 10/1980 Kneifel et al. ........................... 374/8
4,333,333 6/1982 Pangritz ................................... 374/8

Primary Examiner—Charles Frankfort
Assistant Examiner—Patrick Scanlon
Attorney, Agent, or Firm—Wenderoth, Lind & Ponack

[57] ABSTRACT

A device which simulates the burning of an elongated smoking product such as a cigarette, for testing the combustability of an article. The device includes a rod-shaped resistive heating element, the length and cross section of which are the same as those of the product whose burning characteristics are to be simulated. The heating element may be divided into a plurality of longitudinally aligned heat insulated segments. A plurality of lead wires are successively spaced along the length of the heating element so as to respectively uniformly heat the respective portions of the heating element between the adjacent lead wires when an electric current is applied separately thereto. Circuitry is provided for applying an electric current to successively adjacent portions of the heating element through the lead wires for predetermined periods of time, beginning at one end of the heating element and ending at the other, thereby simulating the burning of a cigarette. In use, the device is placed in contact with the article whose combustability is to be tested while successive portions of the heating element are heated.

15 Claims, 15 Drawing Figures

4,519,716

DEVICE FOR TESTING COMBUSTABILITY

BACKGROUND OF THE INVENTION

The invention relates to a combustability tester for accurately testing the combustability of a chair, bed, quilt, matress, blanket and sheet when contacted by the lighted end of a cigarette, and more particularly, to a combustability tester which includes a heater having a combustion effect similar to that of a cigarette, and a control circuit for the heater.

In a conventional method of testing the combustability of an article, a lighted cigarette is placed on, for example, a chair, in order to determine the combustability thereof. However, the temperature of the lighted end of a cigarette varies depending upon the humidity of the ambient air and the thermal capacity and combustion heating value of the cigarette. The test results can therefore vary greatly depending on ambient conditions and the combustion characteristics of the cigarette. In addition, the cigarette may die out during such a combustability test.

SUMMARY OF THE INVENTION

In accordance with the invention, there is provided a combustability tester which is free from such drawbacks encountered in a conventional method of testing the combustability of articles from a lighted cigarette. The combustability tester, according to the invention employs, instead of a real cigarette, an electric heater as the power source for initiating combustion. The electric heater has a shape similar to that of a cigarette, and includes, for example, a silicon carbide (carborundum) red, not less than four lead wires provided on the rod, a timer, and a change-over switch operatively connected to the timer. In one embodiment, the rod is divided into a plurality of longitudinally aligned mutually heat insulated rod segments and the lead wires are provided at opposite ends thereof. Electric current is applied to the portions of the rod which are defined by the adjacent lead wires, separately in succession by the operation of the changeover switch, to heat the rod accurately from one end toward the other and thereby simulate the burning of a cigarette. By controlling the magnitude of electric current applied to the rod, the temperature thereof can be regulated, so that a combustability test can be conducted at a predetermined temperature.

BRIEF DESCRIPTION OF THE DRAWINGS

These and other aspects of the invention will be better understood from the following detailed description of a preferred embodiment when taken with the accompanying drawings in which.

DETAILED DESCRIPTION OF THE PREFERRED EMBODIMENTS

Figure 1A:
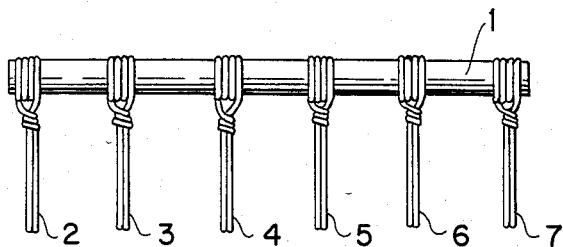
FIGS. 1A and 1B are respectively side and end views of an igniting heater of a tester in accordance with the invention.
Figure 1B:
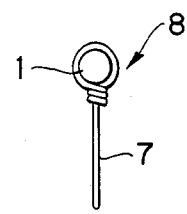

An embodiment of the invention will now be described with reference to the drawings. FIGS. 1A and 1B show an igniting heater 8, and FIG. 2 a control circuit 18 for the heater 8. Referring to FIGS. 1A and 1B, the igniting heater 8 includes a resistive heating element formed, for example, of a silicon carbide (carborundum) rod, the length and thickness of which are substantially equal to those of a cigarette. Lead wires 2, 3, 4, 5, 6 and 7 are provided on the heating element 1 in a spaced manner. In the embodiment shown in the drawings, the lead wires 2-7 are wound successively around the resistive heating element 1. Alternatively, the lead wires may be fastened to the resistive heating element 1 by some other means such as straps. Each of the lead wires 2-7 is formed of a relatively non-oxidizable metal such as titanium, or a Nichrome wire. The resistive heating element 1 is divided into five portions by the lead wires 2-7 as shown in the drawing. When seven volts is applied to each of these portions of the resistive heating element 1 independently, the temperature of the respective portions of the heating element become about 600° C. When the voltage is reduced to 4.2 volts, the temperature of the respective portions of the heating element become about 300° C.

When the relationship between the voltage or amperage used and the temperature of the resistive heating element 1 is determined in advance, a combustability test can be done at a desired temperature even when a means for measuring the temperature of the resistive heating element 1 is not available.

An electric current is applied initially to the portion of the resistive heating element 1 which is between the lead wires 2 and 3 and subsequently to the portion thereof which is between the lead wires 3 and 4. An electric current is then applied in succession to the portions of the resistive heating element 1 which are between the lead wires 4 and 5, 5 and 6, and 6 and 7, at such a rate as to approximate the natural burning rate of a real cigarette.

Figure 2:
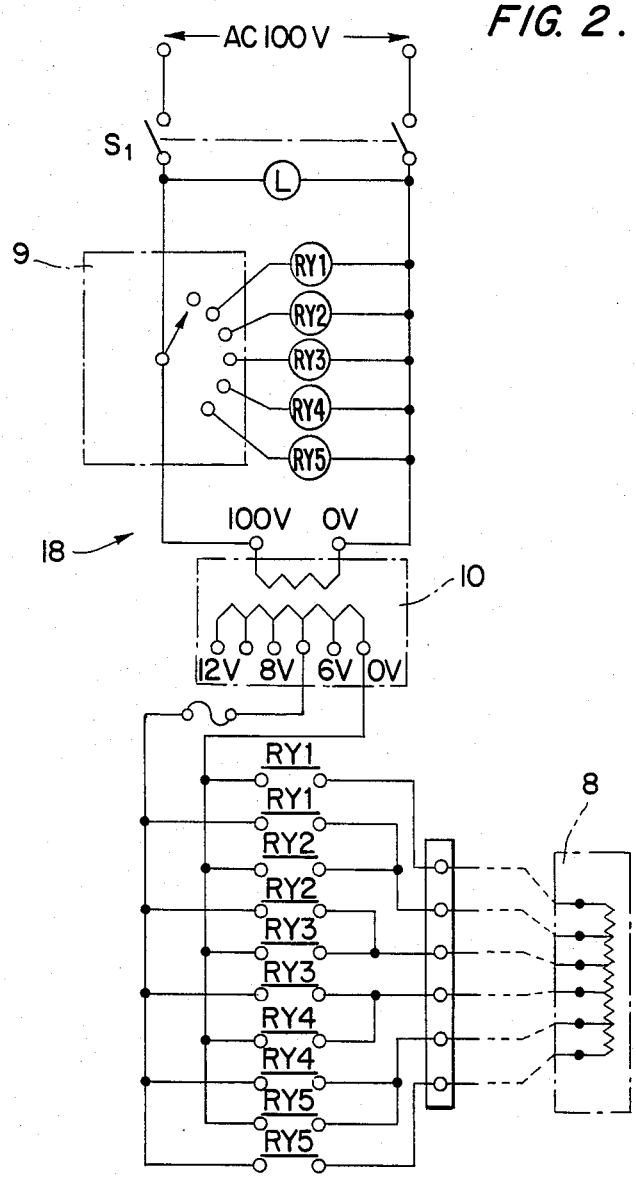
FIG. 2 illustrates a control circuit of a tester in accordance with the invention.

A combustability test is carried out in this matter by using a control unit 13, the circuitry of which is shown at 18 in FIG. 2. Referring to FIG. 2, control circuit 18 includes relays RY1, RY2, RY3, RY4 and RY5 which are shifted at time intervals set by a time switch 9. A transformer in control circuit 18 is provided with taps for transforming an input voltage of 100 volts to 0 to 12 volts. The relays RY1-RY5 are connected to lead wires 2-7 of igniting heater 8 so that the above mentioned divided portions of the resistive heating element 1 can be heated independently in succession.

Figure 3:
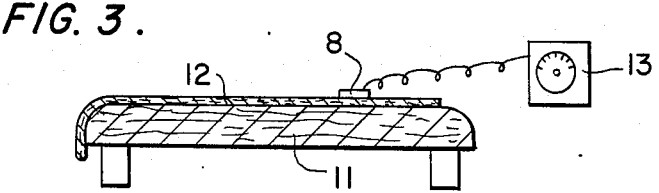
FIG. 3 illustrates how to test the combustability of a bed with the tester of the invention.
Figure 4:
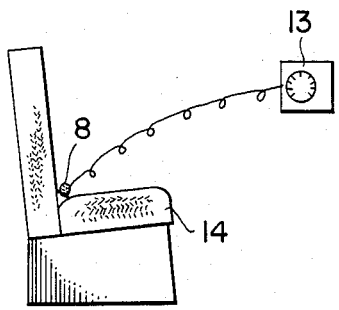
FIG. 4 illustrates how to test the combustability of a chair with the tester of the invention.

The temperature of the resistive heating element 1 is regulated by changing output voltage taps in the transformer 10. FIGS. 3 and 4 illustrate examples of locations on articles whose combustability is to be tested where the heater 8 can be placed during the test. In FIGS. 3 and 4, reference numeral 11 denotes a bed, reference number 12 denotes a blanket, reference numeral 13 denotes the control circuit, and reference numeral 14 denotes a seat portion of a chair.

As a testing procedure, first the relationship between voltages of the transformer 10 and temperatures of the heating element 1 are measured. For example, when input and output voltages of transformer 10 are respectively 60 and 7 volts, a heating temperature of 600° C. can be obtained. Heater 8 is then placed on a sample to be tested. Since a cigarette normally burns in about 20 minutes, the time switch 9 is set so as to shift at intervals of 4 minutes so that the switch will be shifted five times over a 20 minute test period. When the time switch 9 is turned on, one end of the heating element 1 is heated. After 4 minutes have elapsed, a subsequent portion of the heating element is heated. The remaining portions of the heating element are also heated in this manner in succession, so that a simulation of a continuously burning cigarette can be obtained. When, after 20 minutes, the heating operation is completed, the condition of the sample is examined to determine the combustability thereof.

The above is a description of the construction and operation of the invention. An example of a test using the invention will now be described.

Figure 6:
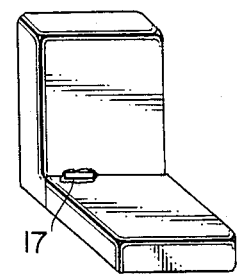
FIG. 6 illustrates the result of a test of the combustability of a chair having a seat covered with vinyl chloride leather using the tester of the invention.
Figure 5A:
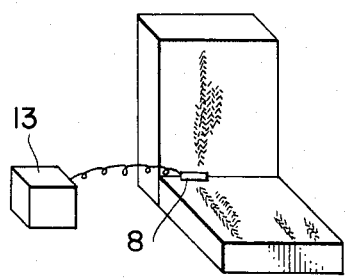
FIGS. 5A, 5B, and 5C are successive views in time illustrating the result of a test of the combustability of a chair having a seat covered with a rayon sheet using the tester of the invention.
Figure 5B:
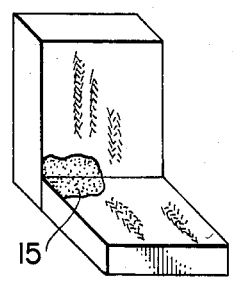
Figure 5C:
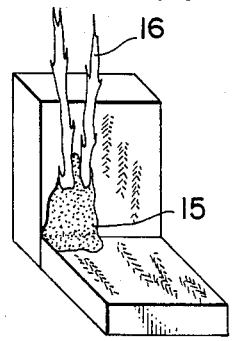

Two urethane foam filled chairs, one having an outer cover of rayon and the other having an outer cover of vinyl chloride leather were prepared. The combustability of these chairs was tested with a tester according to the invention. FIGS. 5A, 5B and 5C illustrate the performance and result of a test of the combustability of the chair having the rayon cover, and FIG. 6 illustrates the result of a test of the combustability of the chair having the vinyl chloride leather cover.

FIG. 5A illustrates the condition of the chair having the rayon cover prior to the application of an electric current to the heater 8 which is set thereon. FIG. 5B illustrates the condition of the chair with the heater 8 removed therefrom just after 20 minutes have elapsed during which time period an electric current had been applied to the heater 8. In the stage of combustion of the chair shown in FIG. 5B, the chair is smoldering except for a combustion-carbonized portion 15 thereof. FIG. 5C illustrates the condition of the same chair in a stage of combustion which is subsequent to the stage of combustion shown in FIG. 5B, in which a flame 16 has occurred and has spread. When the chair having a vinyl chloride leather cover was subjected to the same test, only a small blackened portion 17 was left thereon and no flames had occurred long after the period of application of an electric current to the heater 8 had been completed.

The above tests were performed a second time, and similar results were obtained.

On the other hand, similar combustability tests were also performed by a conventional method using lighted cigarettes, but the same heating conditions could not always be obtained due to the variance of the quality of the cigarettes used and variations in the ambient conditions. Therefore, the reproducability of the conditions of heating were low. Moreover, during some test runs the cigarette died out during the test.

The heater in the tester according to the invention permits an article to be heated at a constant heating value. In particularly, the tester permits tests for the combustability of articles to be reliably and efficiently conducted under various constant conditions, so that accurate results can be obtained.

Figure 7:
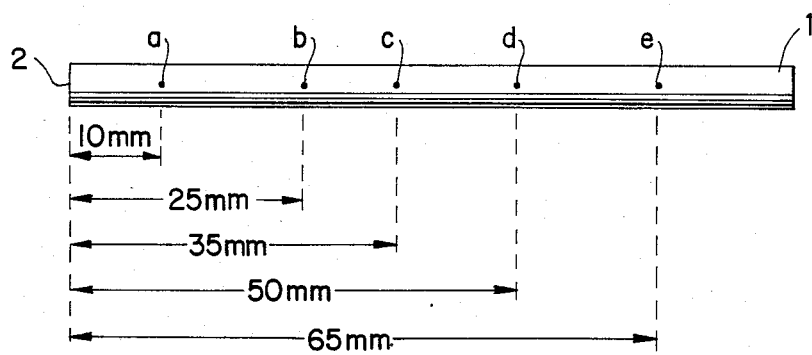
FIG. 7 is a schematic illustration of a cigarette.
Figure 8:
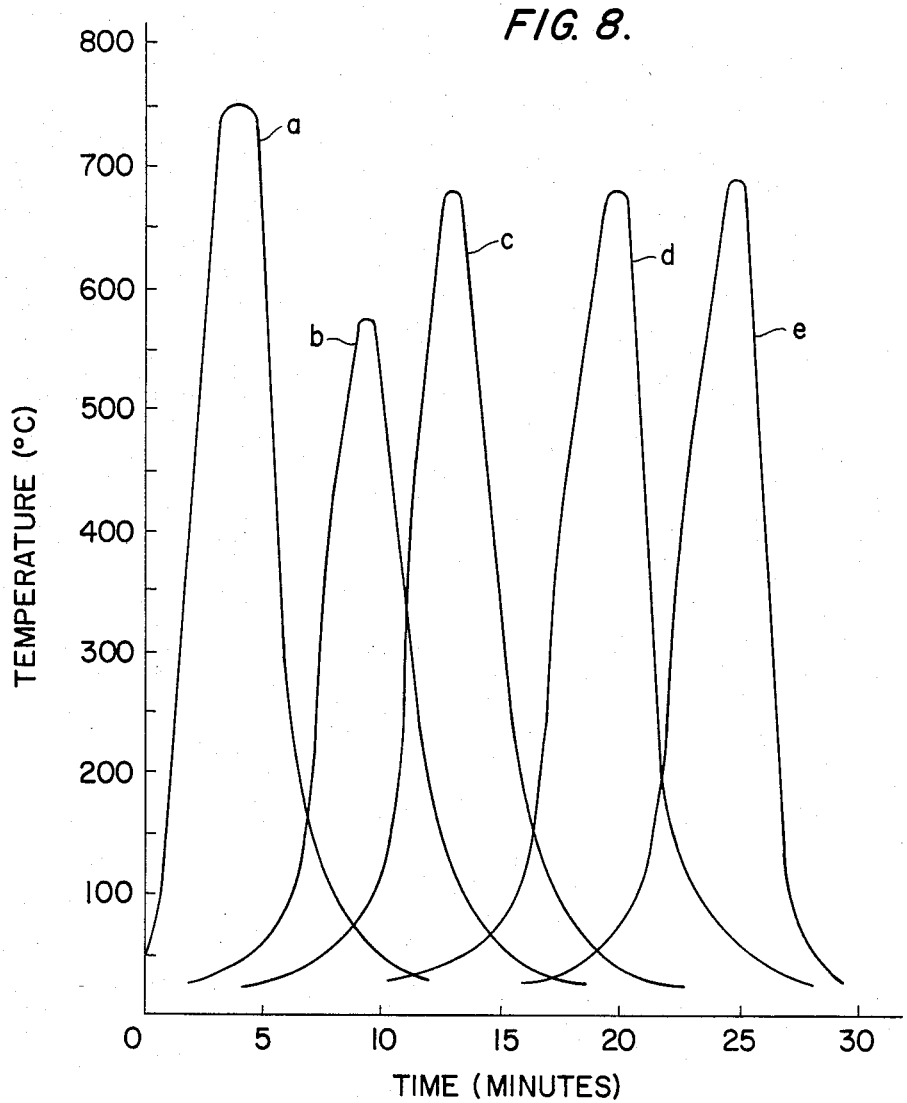
FIG. 8 is a graph showing the temperature of the cigarette shown in FIG. 7 at points along its length as it burns.

FIG. 7 illustrates an 80 mm length cigarette. Measurements of the temperature at various points a, b, c, d and e along the length of the cigarette had results which are illustrated by the graph shown in FIG. 8. As is indicated in FIG. 8, the temperature of the cigarette at each of the points a, b, c, d and e reach a sharp peak as the cigarette burns at the respective points and then dies off quickly.

Figure 9:
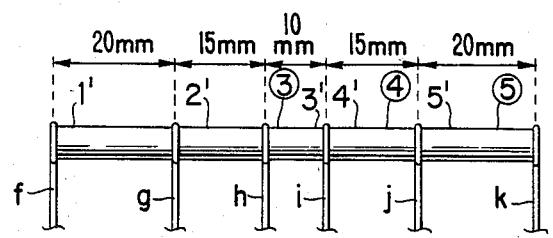
FIG. 9 is a side view of another embodiment of the igniting heater in accordance with the invention.
Figure 10:
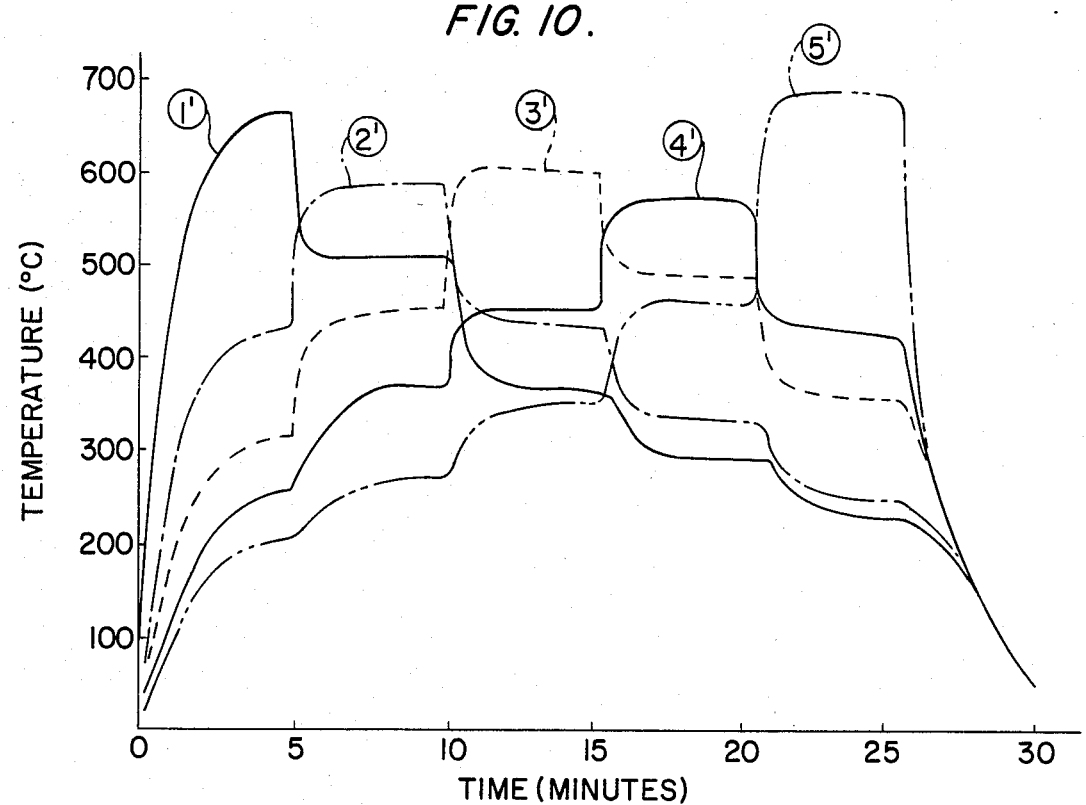
FIG. 10 is a graph showing the temperature of the segments of the heater of FIG. 9 as a function of time.

In an embodiment of the invention similar to that illustrated in FIG. 1A, but in which the lead wires f, g, h, i, j and k are unequally spaced along the length of the silicon carbide rod, predictable temperature variations occur along the length of the rod as a function of time during the use thereof. However, the heating of one segment of the rod also heats to a lesser degree other segments of the rod. As a result, the time variation of the temperature of the segments of the rod is not like that of an actual cigarette but rises and falls shortly in the manner illustrated in FIG. 10, wherein the circled reference numerals 1' – 5' designates the time variation of the temperature of the corresponding segments 1'-5' of the rod illustrated in FIG. 9.

Figure 11:
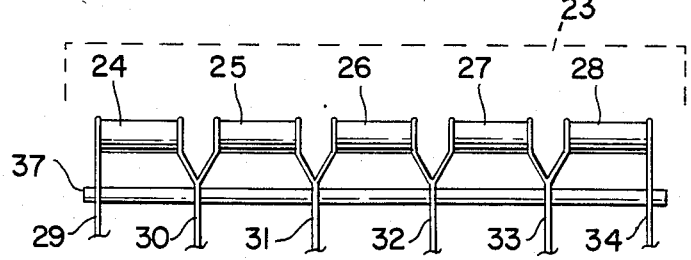
FIG. 11 is a side view of still another embodiment of the igniting heater in accordance with the invention.
Figure 12:
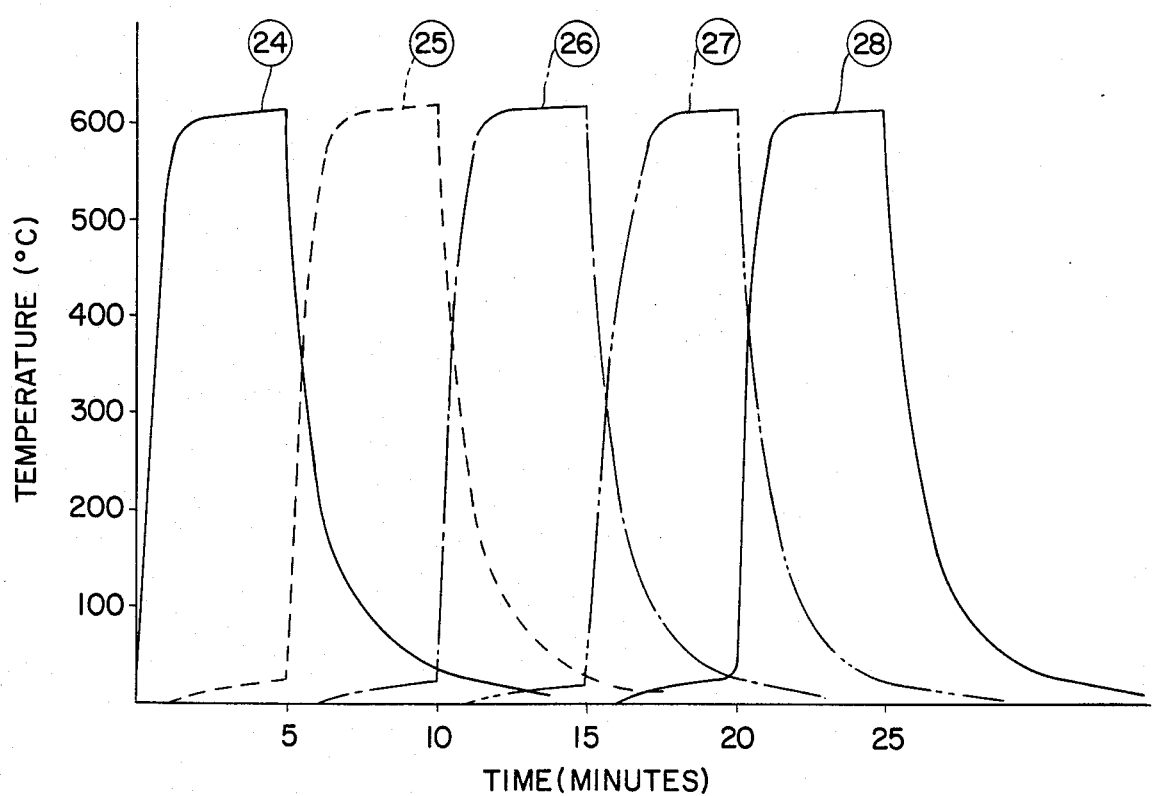
FIG. 12 is a graph showing the temperature of the segments of the heater of FIG. 11 as a function of time.

In order to more closely approximate the actual time variation of temperature of an actual cigarette, the segments of the rod between lead wires can be separated by a space which functions as a thermal insulator between the segments. Thus, in the heater 23 of FIG. 11, lead wires 29, 30, 31, 32, 33 and 34 are connected to opposite ends of longitudinally spaced rod segments 24, 25, 26, 27 and 28 and are fixed to a nonconductive longitudinally extending rod 37 in order to provide longitudinal rigidity to the heater. As a result, as is illustrated by curves 24 – 28 in the graph shown in FIG. 12, the time variation of the corresponding segments 24–28 of the heater are peaked only while an electric current is being applied thereto, and thus more closely approximate the time variation of temperature of a lighted cigarette along its length. Thus, the embodiment of FIG. 11, in addition to providing more consistent results, closely approximates the time and longitudinally varying temperature characteristics of a lighted cigarette.

While only three embodiments of the invention have hereinabove been described in detail, it is to be understood that many modifications of the invention which would be apparent to one skilled in the applicable art are also contemplated. For example, by simple modifications of the above described circuitry and resistive heater element which simulate a lighted cigarette, well within the knowledge of one skilled in the applicable art, a tester which simulates a lighted cigar or other elongated tobacco or tobacco-like smoking product can be obtained. The scope of the invention is therefore intended to include such modifications and to be limited only by the appended claims.

What is claimed is:

1. A device simulating the burning of an elongated smoking product for testing the combustability of an article, comprising:

a rod-shaped resistive heating element having a first end and a second end opposite said first end, the length and cross section of which are the same as those of a product whose burning characteristics are to be simulated; and means for applying an electric current through successively adjacent portions of said heating element along the length thereof, one portion at a time, for respective predetermined periods of time, beginning at said first end and ending at said second and, such that the temperature of the portion to which the electric current is being applied is approximately equal to a normal burning temperature of the product whose burning characteristics are being simulated.

2. A device simulating the burning of an elongated smoking product for testing the combustability of an article, comprising:

a rod-shaped resistive heating element having a first end and a second end opposite said first end, the length and cross section of which are the same as those of a product whose burning characteristics are to be simulated;

a plurality of lead wires successively spaced along the length of said heating element so as to respectively uniformly heat the respective portions of said heating element between adjacent ones of said plurality of lead wires when an electric current is applied separately thereto; and means for successively applying an electric current to successively adjacent ones of said respective portions of said heating element through said plurality of lead wires for respective pre-determined periods of time, beginning at said first end and ending at said second end.

3. A device as in claim 2, wherein said heating element has the shape and size of a cigarette.

4. A device as in claim 3, wherein said electric current applying means comprises means for heating successively, one at a time, each of said respective portions of said heating element to the temperature of a lighted cigarette.

5. A device as in claim 3, wherein said electric current applying means comprises means for heating successively, one at a time, each of said respective portions of said heating element to temperatures in the range of 300° C. to 600° C.

6. A device as in claim 3, wherein said heating element comprises a silicon carbide rod, said plurality of lead wires being formed of titanium and being electrically connected in successive spaced relation to said silicon carbide rod along the length thereof.

7. A device as in claim 2, wherein said plurality of lead wires comprises at least four lead wires.

8. A device as in claim 2, wherein said plurality of wires comprises six lead wires and said respective portions of said heating element comprises five successively adjacent portions of said heating element.

9. A device as in claim 2, wherein said heating element comprises a silicon carbide rod.

10. A device as in claim 2, wherein each of said plurality of lead wires is formed of titanium.

11. A device as in claim 2, wherein each of said plurality of lead wires is formed of Nichrome wire.

12. A device as in claim 2, wherein said heating element comprises a plurality of rod-shaped rod segments longitudinally spaced along its length, said plurality of wires being successively spaced at opposite ends of said rod segments.

13. A device as in claim 1, wherein said periods of time are equal in length.

14. A device as in claim 1, wherein said adjacent portions are equal in length.

15. A device as in claim 2, wherein said heating element comprises a plurality of rod-shaped rod segments longitudinally aligned and heat insulated from one another, said plurality of wires being successively spaced at opposite ends of said rod segments.

* * * * *